United States Patent [19]

Larsen

[11] Patent Number: 4,964,415
[45] Date of Patent: Oct. 23, 1990

[54] APPARATUS FOR DIATHERMY TREATMENT AND CONTROL

[76] Inventor: Lawrence E. Larsen, 308 Hamilton Ave., Silver Springs, Md. 20901

[21] Appl. No.: 380,524

[22] Filed: Jul. 17, 1989

Related U.S. Application Data

[62] Division of Ser. No. 941,649, Dec. 15, 1986, Pat. No. 4,848,362.

[51] Int. Cl.$^5$ ............................................. A61N 5/02
[52] U.S. Cl. ............................. 128/804; 219/10.55 F
[58] Field of Search ............................. 128/804, 422; 219/10.55 R, 10.55 A, 10.55 F

[56] References Cited

U.S. PATENT DOCUMENTS

| | | | |
|---|---|---|---|
| 3,065,752 | 11/1962 | Potzl | 128/804 |
| 4,108,147 | 8/1978 | Kantor | 128/804 |
| 4,282,887 | 8/1981 | Sterzer | 128/804 |
| 4,332,260 | 6/1982 | Bicher | 128/804 |
| 4,446,874 | 5/1984 | Vaguine | 128/804 |
| 4,528,991 | 7/1985 | Dittmar et al. | 128/804 |
| 4,709,701 | 12/1987 | Weber | 128/804 X |
| 4,848,362 | 7/1989 | Larsen | 128/804 |

FOREIGN PATENT DOCUMENTS 0036040 9/1981 European Pat. Off. ............ 128/804

OTHER PUBLICATIONS

Paglione et al, "27 MHz Ridged Waveguide . . . " Microwave J., vol. 24, No. 2, Feb. 1981, pp. 71-76, 79, 80.
Kantor et al, "A 2450 MHz Sleb-Loaded . . . Application . . . ", IEEE Trend Microwave TT, vol. 28, No. 12, Dec. 1980 pp. 1418-1422.
Guy et al., "Development of a 915 MHz . . . Application . . . ", IEEE Trens MTT, vol. 26, No. 8, Aug. 1978, pp. 550-556.
Bramanti, "Small-Opening Microwave Applicator . . . "Med. & Biol. Eng. & Comput., 1981 19, No. 2, pp. 215-217.
Hand et al, "A Physiologically . . . Bolos for Microwave Heating . . . ", Phys Med. Biol., Mar. 1979, vol. 24, No. 2, pp. 426-431.

Primary Examiner—Lee S. Cohen
Attorney, Agent, or Firm—Laubscher Presta & Laubscher

[57] ABSTRACT

Therapeutic deep heating of musculoskeletal tissues is accomplished with an improved transducer that serves simultaneously to couple the power from the generator into the patient and to sense the therapeutic response for treatment control including a method of manufacture and testing of contact applicators for dielectric heating of musculoskeletal tissue. The applicator has a rectangular waveguide in which dielectric material is placed to reduce the guide wave length to the free space value at the frequency of operation. The noninvasive detection of therapeutic response in muscle tissue to dielectric heating is then used to control the treatment. Both heating and sensing are accomplished by one transducer and one apparatus if dielectric heating is employed. If other forms of heating are used, such as ultrasound, the sensor still occurs but the apparatus must be modified, the modifications including replacement of the high power electromagnetic source with a low power source version.

8 Claims, 6 Drawing Sheets

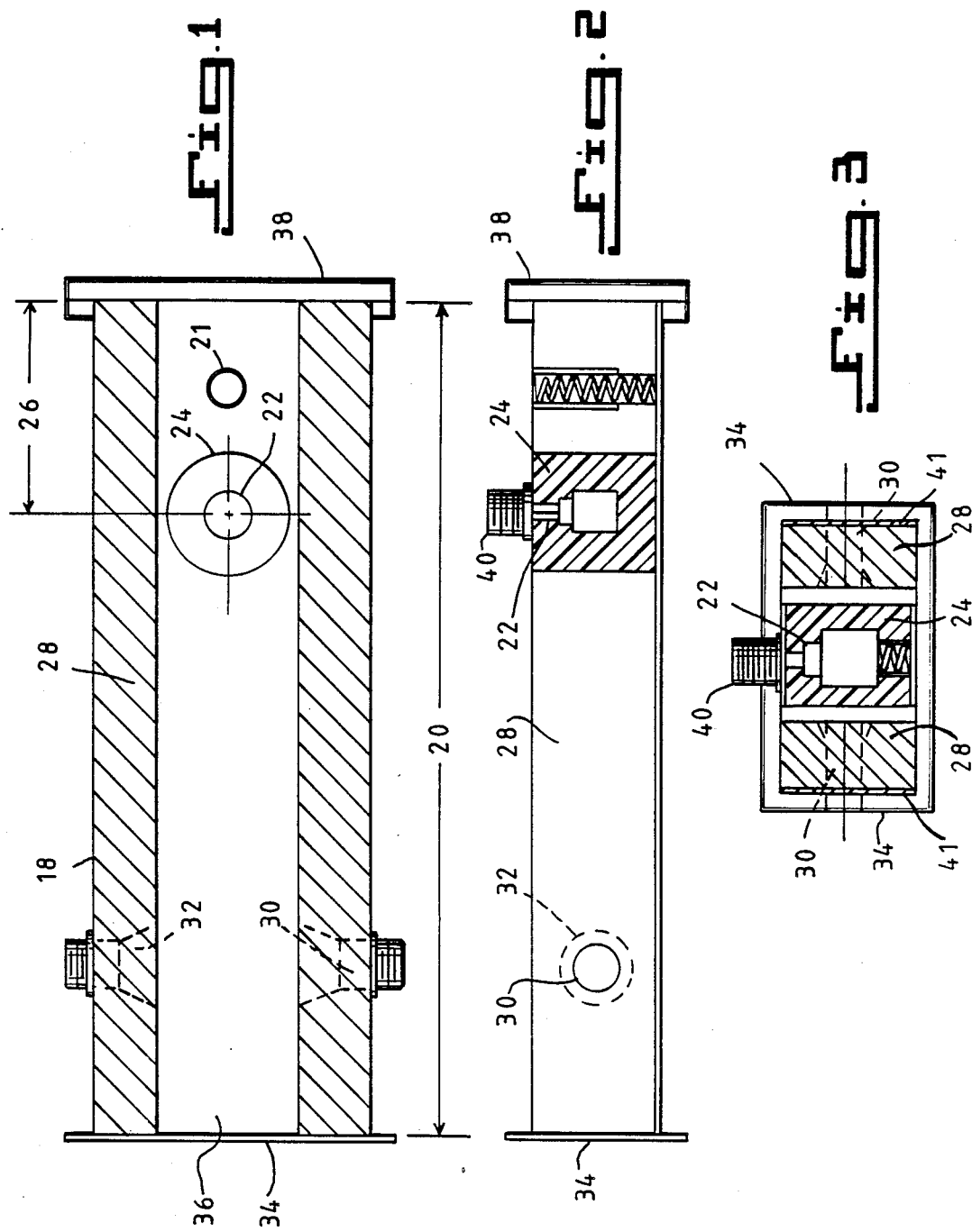

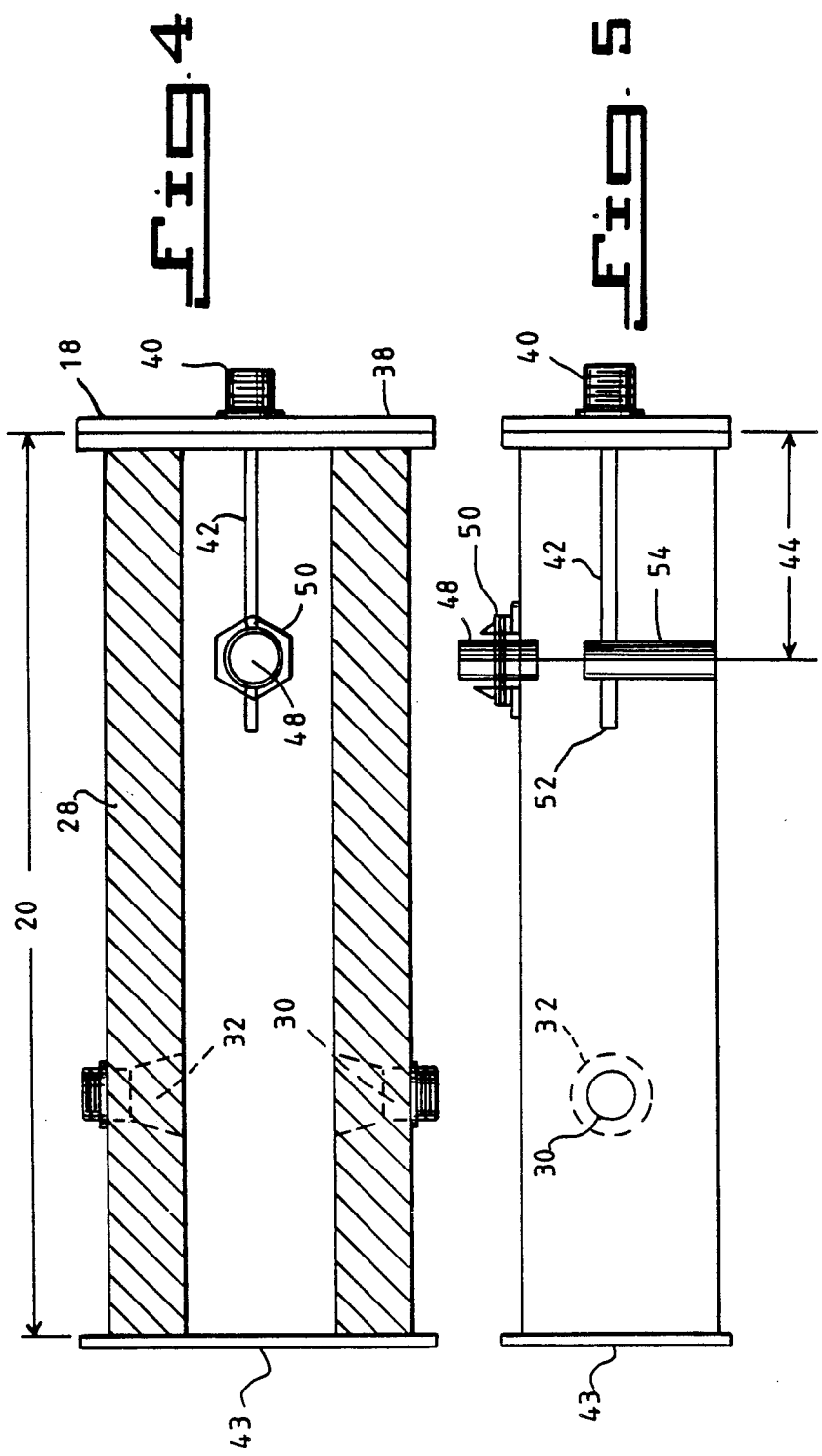

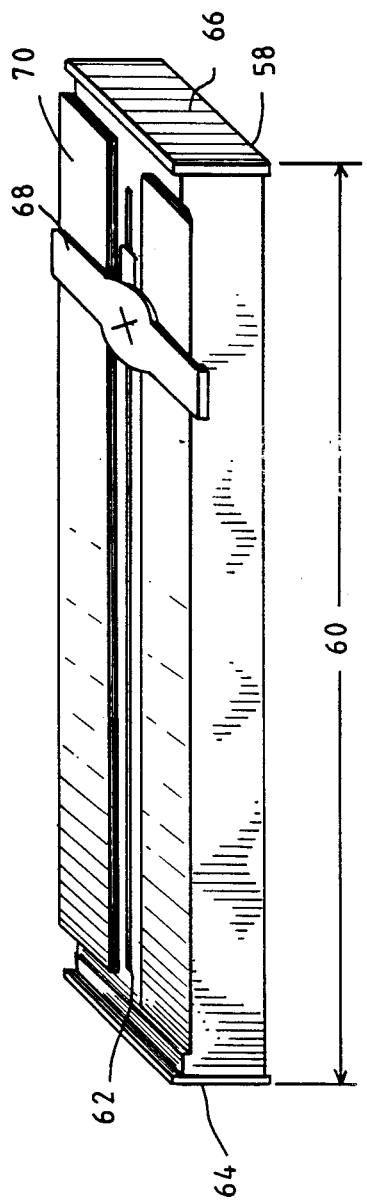
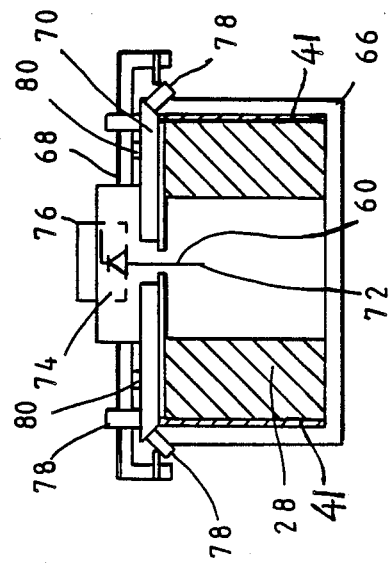
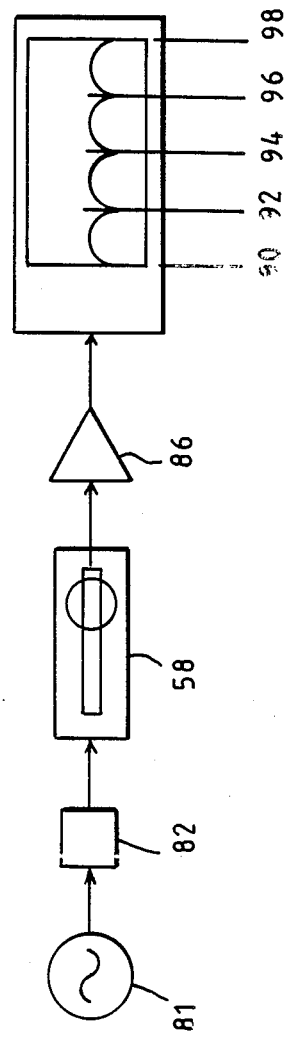

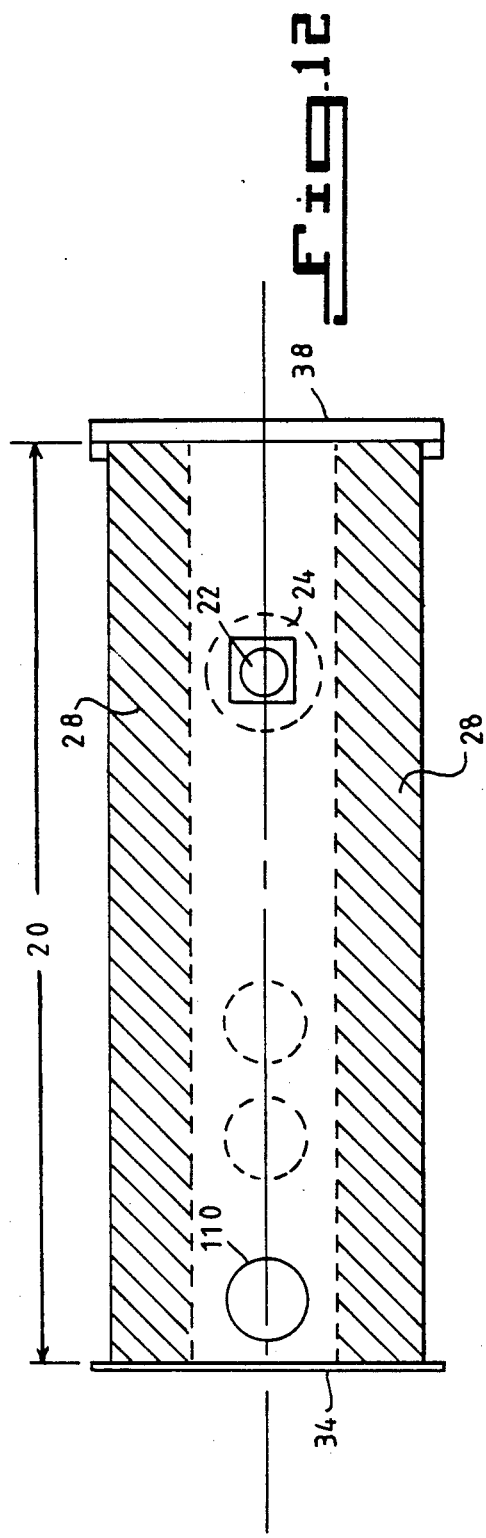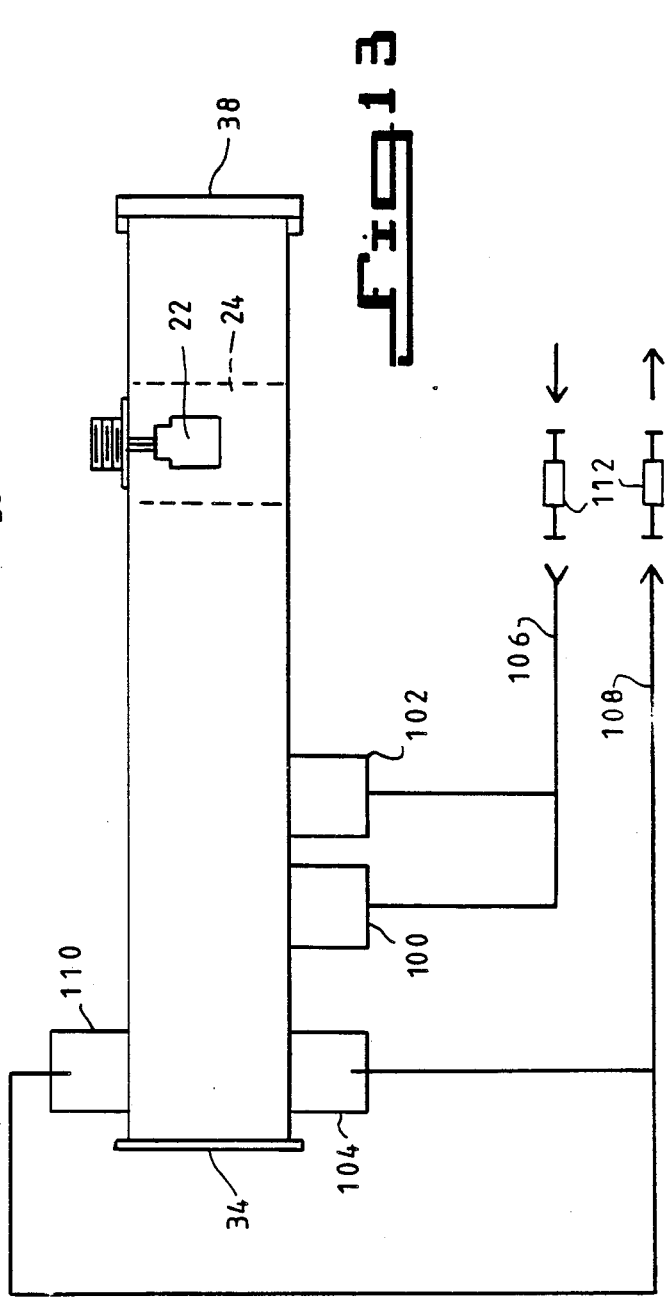

APPARATUS FOR DIATHERMY TREATMENT AND CONTROL

CROSS REFERENCE TO RELATED APPLICATION

This is a division of U.S. patent application Ser. No. 06/941,649 filed Dec. 15, 1986 now U.S. Pat. No. 4,848,362.

FIELD OF THE INVENTION

This invention relates to a transducer and apparatus for deep heat therapy in the treatment of musculoskeletal disorders, and more particularly to low leakage radio frequency (RF) contact applicator design with skin and subcutaneous cooling, applicator manufacturing, including applicator testing for quality assurance, and for detection of therapeutic response to achieve treatment control that may use the same transducer simultaneously for effector and sensor functions.

BACKGROUND OF THE INVENTION

That dielectric heating of musculoskeletal tissue is more efficacious and more efficiently accomplished by contact applicators was established by Kantor, U.S. Pat. No. 4,108,147.

Subsequent improvements deal with broad band tuning to accomplish efficient transfer of microwave energy from applicator into tissue over a wide band of frequencies, and cooling using air as well as water, or convective as well as conductive.

A slotted, metallic cover over the radiating aperature of a waveguide applicator was the subject of the Potzl patent, U.S. Pat. No. 3,065,752.

Vaguine in U.S. Pat. No. 4,446,874 made claims concerning coupling and tuning involving discoupling input coupling of the magnetic loop whereby the frequency of operation and input match are adjusted The design procedures cited in the referenced patents were not viable because these procedures did not provide for compensation and control of evanescent modes in the waveguide applicator. These modes exist principally in the area of the feed that couples microwave energy from the generator via a coaxial cable into the applicator, and on into the patient.

As a result of these modes, the guide wavelength is not equal to the free space wavelength at the frequency of operation, i.e. the TEM mode referred to by Kantor in U.S. Pat. No. 4,108,147 is not necessarily established. The TEM mode cannot exist in a hollow tube waveguide, nevertheless, uniformity of the electric field across the aperture can be improved when the guide wave length is shortened to that of the free space by the use of partial filling with dielectric material parallel to the narrow wall of the guide.

The reduction of the guide wavelength to the free space value is, therefore, a necessary, but not a sufficient condition to accomplish more nearly uniform electric fields across the aperture. Although the guide wavelength may also be shortened by partial filling by dielectric parallel to the broad wall, this does not yield the uniform electric field distribution across the aperture.

The instant invention shows that the length of the dielectric material in the waveguide applicator must also be an appreciable fraction of a wavelength in order to establish the desired guide wavelength and provides for confirmation of the guide wavelength and methods of quality assurance; no methods for confirmation of the guide wavelength or for quality assurance exist in the prior art.

Additionally, this invention establishes the relationship between aperture electric field distribution, guide wavelength, and specific absorption rates at depth sites, none of which is provided for by the prior art.

The instant invention also improves air cooling methods of prior designs which were non-contacting in order to allow egress of air over the patient's skin. The necessary spacing promoted RF leakage as well as tuning variation as the air gap varied with breathing or other motions. RF leakage was not controlled at the point of air ingress and the simple propeller fan mounted within the applicator of the prior design introduces undesirable vibration that modulates the match by alteration of the air gap.

The invention provides for detection of therapeutic response to control dielectric heating during the treatment. Until this invention, no specific individual treatment response has been possible. Prior art was subjective, and at best, the manufacturer provided tabled standards of power and duration for the general population which failed to accomodate for the variations between individuals and were no more than general recommendations. The instant invention makes use of the increase in local blood flow in muscle consequent to local temperature elevation and wave impedance change due to the change in tissue electrical properties, i.e., the instant invention both provokes and detects reactive hyperemia which is the therapeutic response.

The technology of combined microwave heating with sensing has been recognized in other areas. The Furihata patent, U.S. Pat. No. 4,409,993, addressed the need to control dose in an endoscopic device that uses microwave power to heat cancerous tissue to the point of eschar as verified by optical visualization of necrosis. The Converse patent, U.S. Pat. No 4,312,364, and its progeny, the Carr patents, U.S. Pat. Nos. 4,346,716 and 4,557,272, use microwave radiometry to sense heating from an exogenous microwave source.

The instant invention uniquely provides for both heating and sensing of the therapeutic response through the dual use of an antenna. No prior art utilizes the combined effector/sensor action of the instant invention, using the change in complex permittivity of the target tissue due to local vasodilation, nor were the prior methods based on a closely coupled antenna whereby antenna impedance alterations are used to infer changes in the wave impedance of the tissue secondary to the desired reactive hyperemia. Prior technology did not use the critical guide wavelength, design methods, a radome, or surface cooling incorporated as with the instant invention.

SUMMARY OF THE INVENTION

This invention provides new, improved treatment apparatus for dielectric heating as a therapy for musculoskeletal disorders. Implemented are improved methods for contact applicator design which produce more nearly uniform heating in the transverse plane, greater depth of microwave penetration, and apparatus construction which can utilize a dual role of the transducer for both application of power as well as a transducer for sensing the therapeutic response during the treatment without interruption of power delivery.

Quality assurance provides for guide wavelength verification, input match as a function of frequency as well as guide wavelength, and air cooling of the skin which has eliminated spaced applicators and does not promote RF leakage.

A thin radome with a dielectric constant approximately that of subcutaneous fat is employed to interface the applicator to the patient. The radome serves to both prevent fringe field coupling to the patient (leading to excessive heating at the narrow walls of the wave guide where they would otherwise contact the patient), and to provide a low thermal impedance between the air cooling that is applied on its inner surface and the patient's skin that is in contact with its outer surface.

The invention provides for use of the applicator additionally as a sensor for detection of therapeutic response, and use of the sensor response to control the dielectric heating treatment on an individual basis. This is accomplished by measurement and control of the net power absorbed at a level sufficient to produce the desired therapeutic response of increased muscle blood flow. The increased muscle blood flow is a reactive hyperemia in response to temperature elevation. Local temperature elevation in the muscle provokes local vasodilation, opening capillary beds and arterioles. The desired therapeutic response is this reactive hypermia, i.e., increased local blood flow which promotes, for example, resolution of inflammatory infiltrates. The detection of reactive hyperemia also provides an indirect and qualitative measure of muscle temperature in the pattern of the applicator since the local vascular response is triggered at temperatures near 40 degrees centigrade.

An object of this invention is to provide improved treatment apparatus for dielectric heating as a therapy for musculoskeletal disorders.

Another object of this invention is to use increased muscle blood flow which is reactive hyperemia in response to temperature elevation.

Yet another object is to provide a contact applicator design that produces more nearly uniform heating in the transverse plane.

A further object of this invention is to provide an apparatus for treatment which facilitates treatment at greater depths of penetration.

Still another object of this invention is to provide apparatus which acts as both a transducer for application of power, as well as a transducer for sensing the therapeutic response, reactive hyperemia, during the treatment.

Yet another object of this invention is to permit sensing of therapeutic responses without interruption of power delivery.

A further object of this invention is to provide for optimization of the critical parameter of guide wavelength and for the quality assurance for each applicator that includes input match as a function of frequency as well as actual guide wavelength.

Yet another object of this invention is to provide for air cooling of the skin that does not require a spaced applicator and does not promote RF leakage.

It is also an object of this invention to employ a thin radome with a dielectric constant near that of subcutaneous fat to interface the applicator to the patient.

It is a further object of the invention to provide a thin radome to interface the applicator to the patient which prevents fringe field coupling to the patient that normally leads to unwanted heating at the narrow walls of the wave guide where they would otherwise contact the patient.

Yet another object of the invention is to provide a thin radome to interface the applicator to the patient which yields a low thermal impedance between the air cooling that is applied on its inner surface and the skin of the patient that is in contact with its outer surface.

Another object of the invention is to use an applicator as a sensor for detection of therapeutic response, reactive hyperemia, as a means to control the dielectric heating treatment on an individual basis.

Further objects and advantages of this invention will become more apparent in light of the following drawings and description of the preferred embodiments of the invention.

BRIEF DESCRIPTION OF THE DRAWINGS

FIGS. 1, 2 and 3 are the top, side and end orthographic projections, respectively, of one configuration of a preferred embodiment of the invention for applicator/sensor showing a monopole type of electric field feed as the coax to waveguide adapter;

FIGS. 4 and 5 are top and side orthographic projections, respectively, analogous to FIGS. 1 and 2 above, of another embodiment using a magnetic field feed in the form of a shorted loop;

FIGS. 9 and 10 are a perspective and an end projection, respectively, of one configuration of a preferred embodiment of the invention which is used for manufacturing quality assurance, e.g., to establish the guide wavelength at the critical value;

FIG. 11 is a functional block diagram of the quality assurance apparatus;

FIGS. 12 and 13 are analogous to FIGS. 1 and 2, respectively, with added functional block detail showing the method and apparatus for gas cooling and the means for suppression of RF leakage;

DESCRIPTION OF THE PREFERRED EMBODIMENTS

Figures 6, 7, 8:
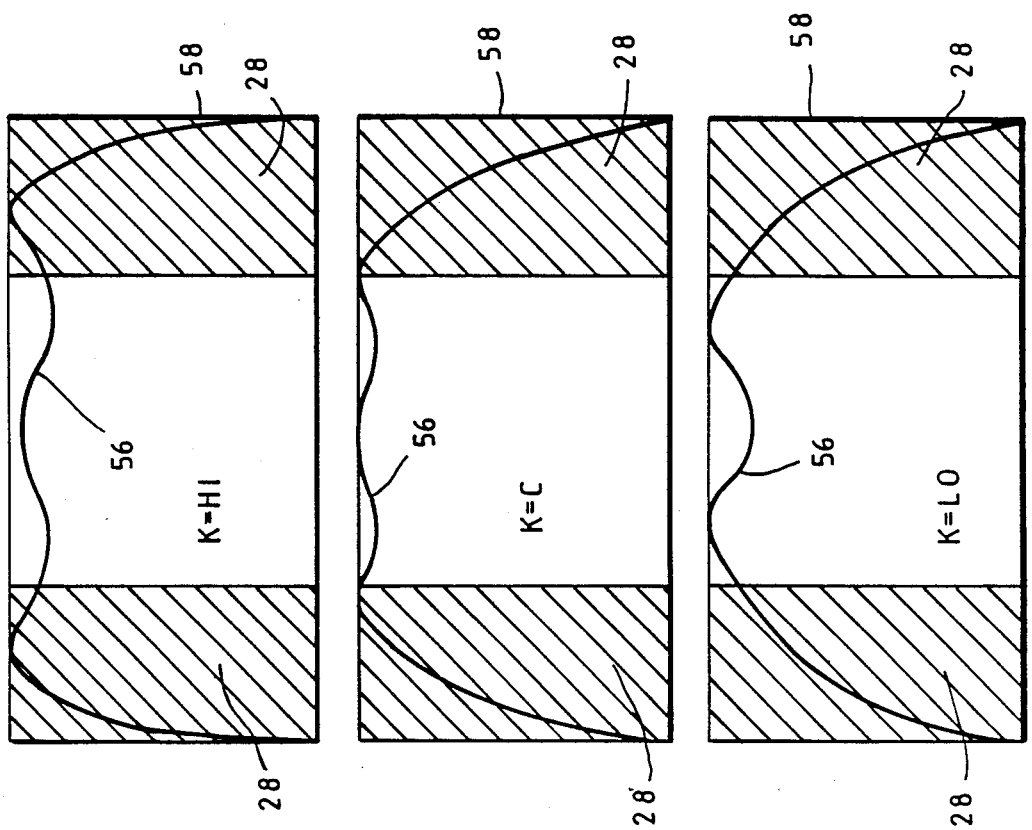
FIGS. 6, 7 and 8 illustrate a high dielectric constant (above critical value), the critical value dielectric constant, and a low dielectric constant, respectively, in diagramatic views of the waveguide showing the expected electric field distribution in the dielectric material and air filled portion of the waveguide.

Referring to the drawings, FIGS. 1, 2 and 3 generally depict a typical applicator 18 of length 20, to be substantially equal to one wavelength at the free space phase velocity, an electric field feed 22, encased in a polystyrene cylinder 24, placed at a distance 26 of one quarter of the guide wavelength (previously established to be equal to the free space wavelength at the frequency of operation).

The high dielectric constant ($k'=10$) and low loss (tan delta=0.002) ceramic (>96%Al1 203) material 28 is placed against the narrow walls of the waveguide 36 and held by mechanical fasteners 30 to the narrow wall. The access to the mechanical fixation on the inside of the applicator is closed by a ceramic plug 32 of substantially the same dielectric properties as material 28, and a thin, e.g. 0.030", radome 34 fabricated from high thermal conductivity material such as Kapton or composite (e.g. G10 with a $k'=4$ and oriented such that the fiber is cross polarized to the electric field in the waveguide 36).

The input match is tuned by means of the depth of penetration of the cylindrical feed 22 into the waveguide 36. An optional spring loaded inductive post tuning device 21 is placed between the feed 22 and the short circuit 38.

There is a connector 40 for the coax cable transmission line from the generator. Only coarse tuning to a return loss of less than 10 db is effected by use of the tuning device 21 with the radome 34 of the applicator being in contact with simulated fat and muscle phantom prepared according to the methods of prior art. A selected gap is produced by low loss dielectric shims 41.

Provision for tuning the input impedance to the source are also shown in FIGS. 1, 2 and 3. The thickness of the longitudinal dielectric material is selected to produce a critical guide wavelength in a test fixture. Small adjustments in the guide wavelength are made by the insertion of low loss shims 41 between the narrow wall and the dielectric to shorten the guide wavelength.

A second embodiment is shown in FIGS. 4 and 5 which are the top and right side orthographic projection analogous to FIGS. 1 and 2 above. The length 20 of the applicator 18 and the dielectric material 28 is substantially one wavelength at the free space phase velocity. The feed 42 is a magnetic loop shorted at a quarter guide wavelength 44. It is tuned for input impedance by a capacitive shaft 48 and shaft lock 50.

This is preferable to a tuning screw since the shaft lock 50 is a collet and clamp that make more reproducible RF ground than a jamb nut and screw. Another degree of tuning is provided by a stub 52 extending from the post 54. Only coarse tuning to a return loss less than 10 db is effected by the use of the tuning device with simulated fat and muscle against the radome 43.

FIGS. 6, 7 and 8 illustrate the conditions of guide wavelength shorter than the critical value, that for the critical value (the free space value), and guide wavelength longer than the critical value, respectively and represent the electric field distribution 56 in the transverse E plane of guide 58. Use of the design procedure from Kantor and/or Turner will result in the condition shown in FIG. 8 where the electric field peak is outside of the dielectric material and in the air filled region of the guide. The critical condition shown in FIG. 7 is also the one where specific absorption rates (SAR) are highest at distances in the order of 1 to 3 cm below the fat-muscle interface.

The dielectric material 28 is shown in opposition to the narrow wall of the applicator 18 and of equal thickness, but of three values of dielectric constant (high, critical and low) for purposes of illustration.

The electric field distribution 56 in the transverse plane is effected by the guide wavelength as the latter relates to the critical value. When the dielectric material 28 decreases the phase velocity excessively, in comparison to a guide completely filled with air, it may produce a guide wavelength that is too short and the electric field peak exists inside the dielectric as shown in FIG. 6. If the dielectric material 28 does not sufficiently contract the guide wavelength, i.e., the guide wavelength is too long, then the peak occurs in the air filled portion of the guide as shown in FIG. 8. At the critical guide wavelength, the peak is just inside the dielectric at the air interface as shown in FIG. 7.

A third embodiment is shown in FIGS. 9 and 10 which is the apparatus used with the method for assuring manufacturing quality and optimizing applicator operation. This is composed of a waveguide applicator of twice normal length, shorted at both ends to establish a standing wave, and with a movable carriage/probe to sample the electric field distribution via a narrow slot in the center of the guide as shown in FIG. 9. The test fixture guide is of dimensions equal to the applicator and contains the feed and dielectric material as shown in either of the first two preferred embodiments. The electric field feed, for example, and carriage are shown in cross section in FIG. 10. The instrumentation block diagram shown in FIG. 11 illustrates typical results as well as the selected node-to-node distance.

FIG. 9 shows a test fixture 58 of length 60, twice the length of the applicator, with a narrow slot 62, milled into one broad wall. The test fixture 58 is fitted with dielectric of the same thickness and constitutive properties as that used in the applicator.

The waveguide test fixture interior dimensions are also identical to the applicator 18 in the transverse plane. The feed is placed at the shorted proximal end 64 whereas the distal end 66 is shorted to produce an electric standing wave pattern as shown in FIG. 11. The standing wave pattern is measured by a carriage assembly 68 that is scanned along a track 70 on either side of the slot 62.

The carriage assembly 68 holds a probe 72 connected to a variable line stretcher 74 and thence to a crystal diode detector 76. The carriage runs on the two piece track 70 by means of conductive wheels 78 and spring contacts 80. This permits scanning the probe 72, at an adjustable, but minimal penetration, over a large fraction of the length of the test fixture 58.

FIG. 11 shows a signal source 81, a low pass filter 82, with a cut-off 10% above the frequency of operation, and the test fixture 58 shown schematically. The feed energized in the test fixture 58 is also identical to that used in the applicator 18. The RF drive produced by the signal source 81 is square wave modulated at an audio frequency and the detector output is amplified by a tuned amplifier 86.

A typical pattern of electric field standing waves is shown as a function of distance from the shorting plate 64 at the feed end. The first null of the test fixture 58 is 90, the second null is 92, and so on to the last null 98 at the distal shorting plate 66. The distance between null 92, and null 94 is used to estimate half the guide wavelength as it would exist in the applicator 18.

Additional null-to-null values, e.g., 94 and 96, are used to establish that the desired mode has been stabilized, i.e. that the undesired evanescent modes are dampened over the distance or length used for the applicator 18. Lengths substantially less than one wavelength are not sufficient to accomplish the desired mode selection.

Furthermore, the specific absorption rate (SAR) produced at various depths in a bilayer phantom comprised of 1 cm of simulated fat and 10 cm of simulated muscle is improved as the guide wavelength is adjusted for the critical value. This feature is related to, but different from, the uniformity of transverse heating.

For example, at a given thickness of dielectric material 28 shaped as a taper in the feed region and uniform in the load region, the SARs are significantly lower than those produced by the same thickness in full length as shown in Table I.

TABLE I

| GUIDE HALF-WAVELENGTHS | T$_1$ | T$_2$ | T$_3$ | |
|---|---|---|---|---|
| 238 mm | 77 mW/g | 28 mW/g | 10 mW/g | tapered |
| 212 mm | 111 mW/g | 40 mW/g | 14 mW/g | 1.062" |
| 160 mm | 116 mW/g | 50 mW/g | 16 mW/g | +3/16" |

Notes:
All measurements are distance to node #3 minus distance to node #2 in 24" test fixture with electric field feed.
Location T1 was 12 mm below the fat-muscle interface. This distance is nearly 1/e depth; thus, the SAR at the interface is ca. 2.7 times higher or 208 mW/g for the longest guide wavelength and 313 mW/g for the near optimal guide wavelength. Since the net power was 50 W in all cases, the efficiency of the applicator is about 4 mW/g/Watt for the longest guide wavelength and about 6 mW/g/Watt for the near optimal case. This is a 50% increase in efficiency.
Lastly, the three sites of temperature measurement are 10 mm apart. In the case of the longest guide wavelength, the second site is 36% of the first site and the third site is 35% of the second site. In the case of the near optimal guide wavelength, the second site is 43% of the first site and the third site is 32% of the second site. This implies that the rate of attenuation with depth of propagation is improved with the near optimal guide wavelength for the bilayer fat/muscle model studied here.

The guide wavelength is adjusted by the use of low loss shims 41 to space the dielectric material 28 away from the wall until the critical guide wavelength is established and the SARs increase. The shims 41 must be thin because although the fields are low near the wall, excessive space prevents stable null-to-null distances.

In FIGS. 12 and 13 the supply ducts 100 and 102 are waveguide below cut-off with attenuation of 60 dB at the frequency of operation. They are connected by flexible hose 106 to a remote fan and source of air at a temperature not higher than 23 degrees C. FIGS. 12 and 13 demonstrate the method and apparatus for air cooling while maintaining contact with the patient and the means for supression of RF leakage by the use of waveguide below cut off for cooling gas supply and return ducts.

The return duct 104 and 110 are also waveguide below cut-off and connected to the low pressure side of the fan by flexible hose 108. The supply ducts 100 and 102 are located on one side to leave room for attachment of the applicator to a positioner. The air flow sensor(s) 112 is used to interrupt the power source via fault control 122 in order to not overheat the skin and superficial subcutaneous tissues in the event of fan failure.

Figure 14:
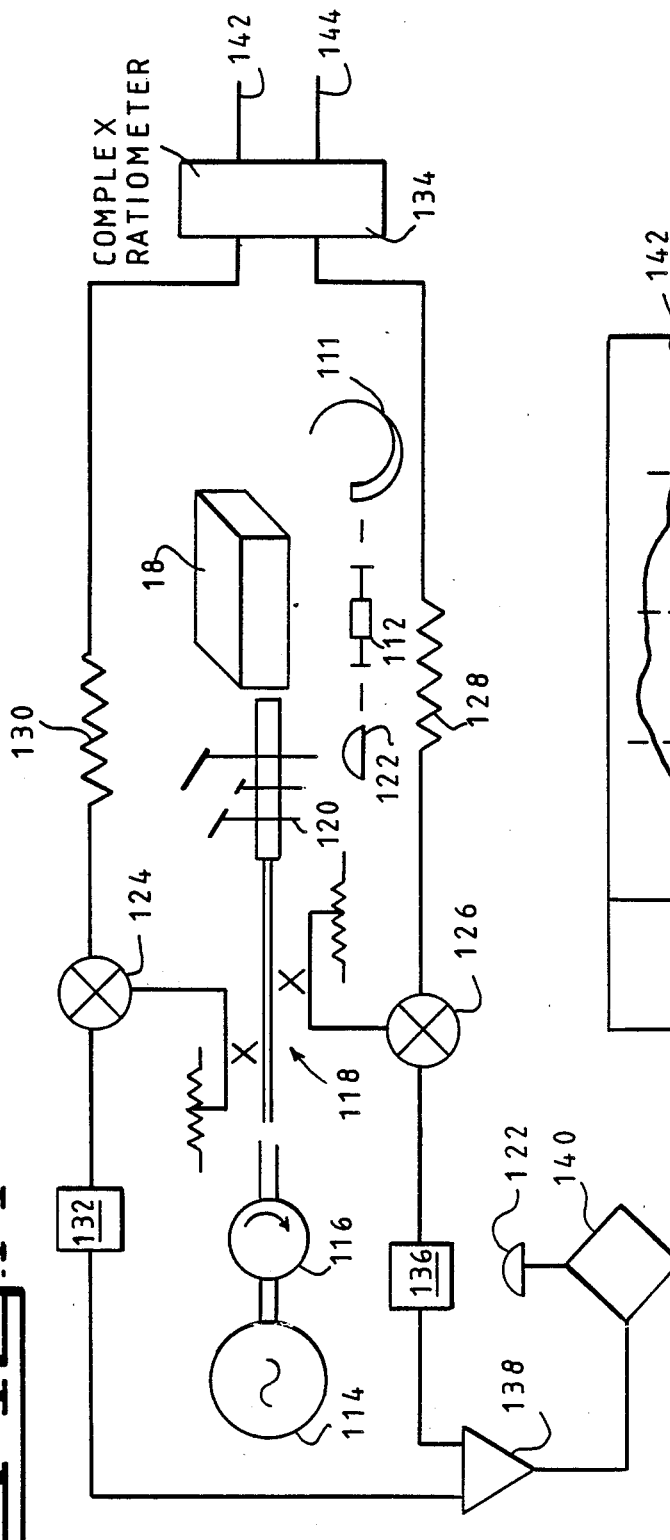
FIG. 14 shows a schematic functional block diagram of the system for the noninvasive detection of the therapeutic response, i.e., reactive hyperemia.

FIG. 14 shows a system for detection of the individual therapeutic response and for treatment control. The method is based on change in the wave impedance of muscle as its blood flow and blood content increase. The change in wave impedance of the muscle is detected by a change in the self impedance of the applicator measured at the terminals of the antenna, or at an integral number of half wavelengths from it, by means of a reflectometer and complex ratiometer. The onset of muscle blood flow is detected by a phase shift in applicator terminal impedance (toward the source) preceded by an increase of the reflection coefficient as the heating takes place.

The power source 114 is selected for frequency stability (1 part/1000 drift) and sufficient power output to produce SARs between 150 and 250 mW/g in bilayer fat/muscle phantoms using the applicator 18. Based on measurements in phantoms and human studies, 30 to 50 watts of CW power are needed. The power source is protected by a three port circulator 116 with a load to protect the power source should the applicator be operated when not matched to or in contact with the patient. The circulator output is connected to the main line of a dual directional coupler 118. The main line continues to a tuner 120, comprised of a stub and a line stretcher then to the applicator/sensor 18. The air flow sensor 112, detects loss of air flow 111 to the applicator/sensor 18, and activates a fault control 122 to interrupt the power source.

The forward and reverse coupled arms are connected to separate power dividers 124 and 126. Attenuation to power levels appropriate for the subsequent instrumentation is accomplished by separate attenuators 128 and 130. When divided, the forward coupled arm enters a bolometer mount, or other power sensor, to measure the forward power via the meter The other half becomes the reference signal for a complex ratiometer 134. The reverse coupled arm after power division is sampled by the reverse power meter 136 and becomes the test channel for the complex ratiometer 134. The forward and reverse powers, 132 and 136, are subtracted in the differential amplifier 138 and displayed by the dosimeter 140 as the net absorbed energy per unit time. Failure to maintain the selected net absorbed energy per unit time also activates the fault control 122 to interrupt the power source. Net absorbed power is used, therefore, for three purposes: (1) to assist regulation of the net energy per unit time delivered to the patient; (2) to establish a very good match to the patient at the baseline power level; and (3) to detect coupling faults.

Tests have shown that a return loss of 30 dB or better is advantageous. Similarly, the directivity of the reflectometer tuner 120 should be 40 dB or better. The tuner 120 is adjusted to maximize the ratio of forward to reverse power by a procedure well known to those skilled in the art. The complex ratiometer produces two output signals as functions of time as shown in FIG. 15, the magnitude 142 and phase 144 of power wave scattering parameter $S_{11}$.

With reference to FIG. 14, if another form of heating is used, such as ultrasound, the sensor functions may still be implemented. The changes in the instrumentation block diagram are to replace the high power generator 114, with a low power source at the same frequency, and to reduce the value of attenuation in attenuators 128 and 130 to be appropriate for the complex ratiometer 134 input levels. For example, the high power source of 30 to 50 watts would be reduced by 30 dB and the attenuators 128 and 130 would be changed for 30 dB less attenuation in order to set proper signal levels at the complex ratiometer 134.

Figure 15:
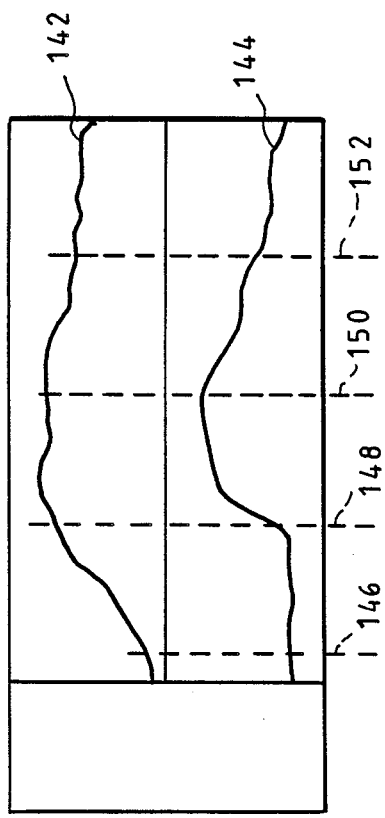
FIG. 15 is a block diagram showing changes illustrating non-electromagnetic heating modalities.

With reference to the complex ratiometer outputs shown in FIG. 15, the time course of the complex scattering parameter discloses biophysical events in the muscle by virtue of the effect of changes in the wave impedance due to the blood flow and blood content of that tissue. Since the applicator/sensor 18 is closely coupled to the tissue being heated, the self impedance of the applicator is effected by the change in wave impedance in the tissue as the blood flow and blood content increase.

The change in applicator/sensor self impedance is monitored at the antenna's terminals, or at an integral number of half wavelengths toward the generator, by changes in the complex reflection coefficient as normalized by the forward wave.

Furthermore, in reference to the complex ratiometer outputs 142 and 144 shown in FIGS. 14 and 15, the observed changes in the magnitude of $S_{11}$ recorded over time in as 142 are a gradual increase in the magnitude, without a significant change in phase, as the tissues heat. These events are illustrated at time reference 146 when the specified net energy per unit time is first established. The latency, time at 148 minus time at 146, to onset of phase shift 144 is shown in rectangular coordinates. The end of power application is shown at 150 and start of the range of motion/strength exercises during the cooldown period at 152 is also shown in FIG. 15.

In terms of a polar display of $S_{11}$ the magnitude increases substantially along a radius of constant phase. As the change of magnitude approaches a plateau, a latency of several minutes, shown at 146 and 148, is required before the phase rotates toward the generator on the Smith chart.

This phase rotation often takes place coincident with a reduction in the subjective feeling of deep heat. This sequence of events takes typically 10 to 20 minutes at the stated reference SARs. The latency, time at 148 minus time at 146, corresponds to the time necessary to elevate muscle temperatures to the point where local vasodilation takes place. At that point, the phase rotation takes place with characteristically small additional changes in magnitude.

Whereas certain specific embodiments of the improved apparatus for deep heat treatment of musculoskeletal disorders have been disclosed in the foregoing description, it will be understood that various modifications within the scope of the invention may occur to those skilled in the art.

Therefore, it is intended that adaptations and modifications should be comprehended within the meaning and range of functional equivalents of the preferred embodiments. For example, changes in material and dimensions that are subsumed in the teaching of the instant patent may be used in place.

Likewise the display options for detection of the therapeutic response may use any of the equivalent parameters of impedance, reflection coefficient, scattering parameters $S_{11}$, or admittance displayed in rectangular or equivalent polar co-ordinates or coordinate transformations such as the Smith chart or Carter chart.

Similarly broader bandwidth (10% to 20%) impedance matching may be employed to augment the narrow band reactive tuner as is well known to those skilled in the art.

What is claimed is:

1. Apparatus for deep heat treatment of musculoskeletal disorders, comprising
   (a) a radio-frequency wave guide applicator and sensor (18) for producing therapeutic deep heat and for detecting a therapeutic response thereto; and
   (b) means (58) for adjusting said applicator and sensor to an optimum wavelength, said adjusting means including
      (1) a wave guide having transverse dimensions corresponding with those of said applicator and sensor;
      (2) dielectric blocks (28) arranged within said wave guide;
      (3) means (81, 82) connected with one end of said wave guide for energizing said wave guide to produce a wavelength therein, said wave guide being energized at the frequency at which said wave guide applicator and sensor is energized;
      (4) means (74) for sensing the wavelength within said wave guide along the length thereof;
      (5) means (41) for adjustably spacing said dielectric blocks from the walls of said wave guide to produce a critical wavelength therein corresponding to the free space wavelength at the frequency at which said wave guide is energized; and
      (6) means (30) for mounting said dielectric blocks within said wave guide applicator and sensor, the spacing of said blocks within said wave guide applicator and sensor corresponding with the spacing within said adjusting means, whereby the optimum wavelength within said wave guide applicator and sensor is provided.

2. Apparatus as defined in claim 1, wherein said adjusting means wave guide is slotted along the length thereof.

3. Apparatus as defined in claim 2, wherein said wavelength sensing means comprises a probe which extends into said adjusting means wave guide via said slot.

4. Apparatus as defined in claim 3, and further comprising a carriage with which said probe is connected, said carriage being movable along the length of said adjusting means wave guide adjacent said slot.

5. Apparatus as defined in claim 4, wherein said probe includes a crystal detector connected with an amplifier to produce a wavelength output signal.

6. Apparatus as defined in claim 1, wherein said adjustable spacing means comprise dielectric shims.

7. A method for deep heat treatment of musculoskeletal disorders, comprising the steps of
   (a) applying therapeutic deep heat to a patient with a radio-frequency wave guide applicator and sensor;
   (b) optimizing a critical parameter of the applicator and sensor wavelength, including the steps of
      (1) energizing a test fixture having the same transverse dimensions as said applicator and sensor and containing dielectric blocks to produce a wavelength therein, said test fixture being energized at the same frequency as said applicator and sensor;
      (2) sensing the wavelength within said test fixture along the length thereof;
      (3) adjusting said test fixture dielectric blocks to produce a critical wavelength corresponding to the free space wavelength at the frequency at which said test fixture is energized; and
      (4) arranging the dielectric blocks from said test fixture within said wave guide applicator and sensor with the same adjusted spacing as in said test fixture.

8. A method for deep heat treatment of musculoskeletal disorders, comprising the steps of
   (a) providing RF deep heat treatment musculoskeletal apparatus having an RF power source, a combined radio-frequency waveguide applicator and sensor, a dual directional coupler and means for indicating a complex scattering parameter;
   (b) providing a test fixture for use with the combined waveguide applicator and sensor, said fixture and said combined applicator and sensor having corresponding feeds and transverse dimensions;
   (c) using said deep heat treatment musculoskeletal apparatus to induce deep heat treatment to the musculoskeletal part of a person and to detect a therapeutic response of increased muscle blood flow of said person to the deep heat treatment;
   (d) optimizing said therapeutic response by establishing a critical wavelength in said test fixture by positioning dielectric blocks within said test fixture using shims, said critical wavelength being substantially equal to the wavelength at a free space phase velocity of the frequency of operation; and
   (e) transferring said dielectric blocks and shims from said text fixture to said combined waveguide applicator and sensor, thereby to verify said wavelength and account for evanescent modes.

* * * * *